United States Patent
Chen et al.

(10) Patent No.: US 12,296,163 B1
(45) Date of Patent: May 13, 2025

(54) SYSTEM AND METHOD FOR THE ACTIVATION OF ACTIVE ION TRANSPORTERS WITHOUT THE CONSUMPTION OF ADENOSINE TRIPHOSPHATE (ATP) MOLECULES FOR THE TREATMENT OF KIDNEY ISCHEMIA

(71) Applicant: University of South Florida, Tampa, FL (US)

(72) Inventors: Wei Chen, Tampa, FL (US); Ruisheng Liu, Tampa, FL (US)

(73) Assignee: University of South Florida, Tampa, FL (US)

( * ) Notice: Subject to any disclaimer, the term of this patent is extended or adjusted under 35 U.S.C. 154(b) by 560 days.

(21) Appl. No.: 17/697,366

(22) Filed: Mar. 17, 2022

Related U.S. Application Data

(60) Provisional application No. 63/162,169, filed on Mar. 17, 2021.

(51) Int. Cl.
    *A61N 1/32*      (2006.01)
    *A61N 1/08*      (2006.01)

(52) U.S. Cl.
    CPC ........ *A61N 1/32* (2013.01); *A61N 1/08* (2013.01)

(58) Field of Classification Search
    CPC ..................................... A61N 1/32; A61N 1/08
    See application file for complete search history.

(56) References Cited

U.S. PATENT DOCUMENTS

| | | |
|---|---|---|
| 4,165,750 A | 8/1979 | Aleev et al. |
| 8,073,549 B2 | 12/2011 | Chen |
| 2010/0249757 A1* | 9/2010 | Chen ................. A61N 1/32 |
| | | 604/890.1 |

OTHER PUBLICATIONS

Tran et al., "Synchronization Modulation Increases Transepithelial Potentials in MDCK Monolayers through Na/K Pumps," Apr. 2013.PLOS one, pp. 1-9.
Jeon et al., "Effects of Pulse Duration on Muscle Fatigue During Electrical Stimulation Inducing Moderate-Level Contraction," Muscle & Nerve. Apr. 2018, pp. 1-8.
Mckenna et al., "Muscle K+, Na+, and Cl-disturbances and Na+-K+ pump inactivation: implications for fatigue," J Appl Physiol. Oct. 2007.
Liang, "The modified Synchronization Modulation technique revealed mechanisms of Na,K-ATPase," ProQuest, Mar. 2019. pp. 1-103.

(Continued)

*Primary Examiner* — Joseph M Dietrich
(74) *Attorney, Agent, or Firm* — Molly L. Sauter; Smith & Hopen, P.A.

(57) ABSTRACT

A system and method to control the Na/K pumps for the treatment of ischemia of the kidney by providing an energy generating synchronization modulation electric field that is effective in synchronizing the Na/K pumps down to individual steps throughout the pumping cycle and in synthesizing one ATP for each pumping cycle. The generated ATP molecule compensates the ATP consumed in extrusion of 3 Na ions and pumping 2 K ions, resulting in a net-consumption of ATP for the Na/K pumps controlled by the system and method of the present invention that is significantly reduced, theoretically to zero, thereby providing an effective treatment for ischemia of the kidney.

18 Claims, 9 Drawing Sheets

(56) References Cited

OTHER PUBLICATIONS

Dreibati et al., "Influence of electrical stimulation frequency on skeletal muscle force and fatigue," Annals of Physical and Rehabilitation Medicine 53. Jan. 2010, pp. 1-12.
Chen et al., "Electrical Activation of Na/K Pumps Can Increase Ionic Concentration Gradient and Membrane Resting Potential," J. Membrane Biol. 2007, pp. 1-9.
Taghian et al., "Modulation of cell function by electric field: a high-resolution analysis," The Royal Society. Apr. 2015, pp. 1-11.
Liu et al., "Activation of Na+ and K+ pumping modes of (Na, K)-ATPase by an Oscillating Electric Field," The Journal of Biological Chemistry vol. 265, No. 13, May 1990.
Di et al., "Effects of power frequency electric field exposure on kidney," Ecotoxicology and Environmental Safety. Feb. 2020, pp. 1-7.
Blank, "Na, K-ATPase function in alternating electric fields," The FASEB Journal vol.$ Mar. 2020. pp. 1-5.

\* cited by examiner

Physiological condition

Synchronization Modulation

SYSTEM AND METHOD FOR THE ACTIVATION OF ACTIVE ION TRANSPORTERS WITHOUT THE CONSUMPTION OF ADENOSINE TRIPHOSPHATE (ATP) MOLECULES FOR THE TREATMENT OF KIDNEY ISCHEMIA

CROSS-REFERENCE TO RELATED APPLICATIONS

This application claims priority to currently pending U.S. Provisional Patent Application No. 63/162,169 filed on Mar. 17, 2021, and entitled, "SYSTEM AND METHOD UTILIZING ELECTRICAL ENERGY TO FUEL AND ACTIVATE ACTIVE ION TRANSPORTER WITHOUT CONSUMPTION OF ADENOSINE TRIPHOSPHATE (ATP) MOLECULES: CLINICAL ISCHEMIA APPLICATION ON KIDNEY", which is incorporated by reference herein in its entirety.

BACKGROUND OF THE INVENTION

In living systems there are many active ion-transporters, such as electrogenic pump molecules and active ion-exchangers in cell membranes. These active ion-transporters maintain the specific ionic concentrations in the cell as well as the ionic concentration gradients across the cell membrane, wherein ionic concentration gradients result in an electrical potential across the cell membrane. The ionic concentration gradients and the membrane potential constitute electrochemical potential across the cell membrane, which is critical to many cell functions.

The electrochemical potential is the source for the generation and propagation of the action potential for all of the excitable cells, such as nerve cells, skeletal muscle fibers, and cardiac cells. This electrochemical potential also provides energy to many other active transporters, such as the Na/H exchangers that influence pH value. The ionic concentration gradients also play a significant role in controlling the cell volume and homeostasis. Therefore, maintaining the ionic concentration gradients and the membrane potential is critical to living cells.

The Na/K pump, or Na/K ATPase, is one of the most prevalent house-keeping proteins that is found within the membrane of almost every cell. The Na/K pump extrudes three Na ions out of the cell via the exchange of two K ions and consumption of one adenosine 5'-triphosphate (ATP) during each pumping cycle in order to maintain the ionic concentration gradients and the cell membrane potential. The Na/K pump is a unique energy converter which converts ATP hydrolysis energy to the electrochemical potential difference across the cell membrane so that the membrane proteins can easily use the energy.

Many diseases, or non-physiological conditions, are directly related to dysfunction of the Na/K pump. Exemplary diseases include various cardiac diseases, kidney diseases, especially the ischemia-induced kidney failures and kidney-related hypertension, diabetes induced ulcer, Alzheimer diseases and muscle fatigue.

Since the active ion transporters involve ion transportation across the cell membrane, the transporters are sensitive to the membrane potential. In the last a few decades, significant efforts have been made to electrically control or manipulate the active ion transporters. However, a practical technique is not currently available that can effectively activate the functions of active ion transporters at physiological running conditions. Once the ATP molecules are insufficient, the transporter function will be significantly reduced.

Accordingly, what is needed in the art is a system and method for improves the pumping function of active ion transporters.

SUMMARY OF THE INVENTION

In various embodiments, the present invention provides a system and method for controlling an active transporter by applying a $3^{rd}$ generation synchronization modulation electric field ($3^{rd}$-SMEF), wherein the active ion transporter not only actively extrudes 3 Na and pumps in 2 K ions by consuming one ATP molecule, but also synthesizes one ATP in each pruning cycle so that the ATP consumption is significantly reduced, theoretically to zero.

In one embodiment, the present invention provides a method for controlling active ion transporters for the treatment of kidney ischemia. The method includes, applying an oscillating electric field to one or more active ion transporters of a kidney experiencing ischemia, wherein the oscillating electric field comprises three serially applied phases. Applying the oscillating electric field includes, applying a synchronization phase to synchronize the active ion transporters to a physiological turnover rate of the active ion transporters down to individual steps within a running cycle with a net-consumption of adenosine triphosphate (ATP) substantially equal to zero, applying a modulation phase to modulate the synchronized active ion transporters to a predetermined target turnover rate and applying a maintenance phase to maintain the synchronized active ion transporters at the predetermined target turnover rate for a predetermined duration of time.

In another embodiment, the present invention provides, a system for controlling active ion transporters for the treatment of kidney ischemia. The system includes an electric field generator to generate and apply an oscillating electric field to one or more active ion transporters of a kidney experiencing ischemia, wherein the oscillating electric field comprises three serially applied phases. Applying the oscillating electric field includes, applying a synchronization phase to synchronize the active ion transporters to a physiological turnover rate of the active ion transporter down to individual steps within a running cycle with a net-consumption of adenosine triphosphate (ATP) substantially equal to zero, applying a modulation phase to modulate the synchronized active ion transporters to a predetermined target turnover rate and applying a maintenance phase to maintain the synchronized active ion transporters at the predetermined target turnover rate for a predetermined duration of time.

In an additional embodiment, the present invention provides a computer-readable medium storing a set of instructions configured for being executed by at least one processor for performing a method for controlling one or more active ion transporters of a kidney experiencing ischemia, the method comprising, controlling an electric field generator to apply an oscillating electric field to the one or more active ion transporters, wherein the oscillating electric field comprises three serially applied phases. Applying the oscillating electric field includes, applying a synchronization phase to synchronize the active ion transporters to a physiological turnover rate of the active ion transporters down to individual steps within a running cycle with a net-consumption of adenosine triphosphate (ATP) substantially equal to zero, applying a modulation phase to modulate the synchronized active ion transporters to a predetermined target turnover rate and applying a maintenance phase to maintain the synchronized active ion transporters at the predetermined target turnover rate for a predetermined duration of time.

As such, the present invention provides an energy generating synchronization modulation electric field that can utilize electric energy to effectively fuel the Na/K pumps and activate or deactivate the turnover rate of the pump molecules, without ATP consumption. In specific embodiments, the $3^{rd}$ generation SMEF of the present invention can be used to treat ion transportation dysfunctions, including but not limited to ischemia.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION OF THE INVENTION

Figure 1A:
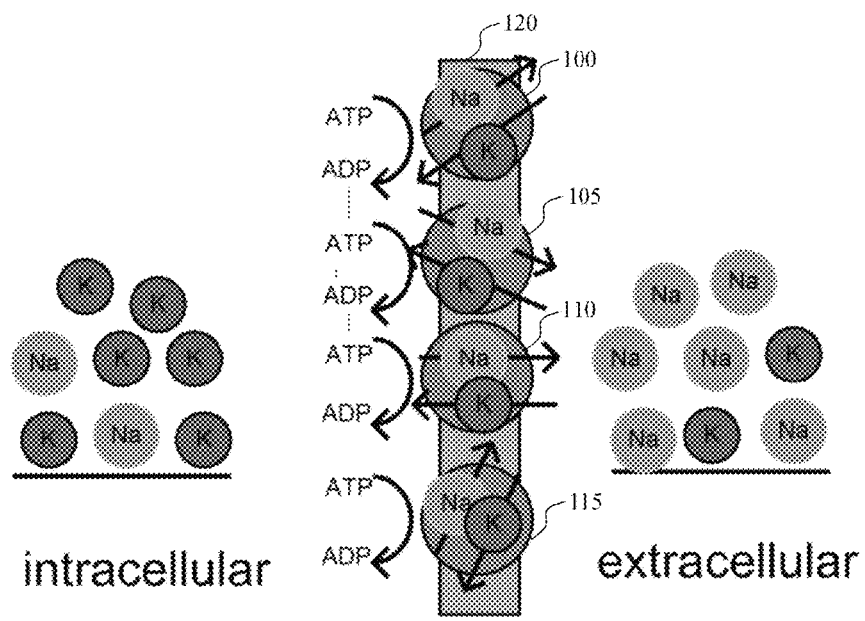
FIG. 1A illustrates random pace pumped molecules, in accordance with an embodiment of the present invention.

In various embodiments, the present invention provides a system and method for controlling an active ion transporter for the treatment of ischemia by applying an improved synchronization modulation electric field which not only drive the transporters to actively transport ions by consuming ATP, but also providing electric energy to the active transporters so that the transporter can synthesize one ATP in each running cycle. As a result, the electric energy substitutes the ATP hydrolysis energy to fuel the active ion transporter to actively transport ions across the cell membrane, without requiring ATP consumption.

Sodium-potassium (Na/K) pumps are known in biology to be one of many active ion transporters. In the following detailed description, the Na/K pump is used as an example of the process for controlling an active ion transporter. However, the description does not require any specific characteristics of the pump molecules, thus it is within the scope of the present invention to control other active ion transporters by the specially designed energy generating synchronization modulation electric field, as described.

Na/K ATPases, or Na/K pump, is a prevalent active transporter in almost all kinds of cells. In operation, the pump extrudes 3 Na ions by exchanging 2 K ions to build up Na and K concentration gradients and the potential difference across the cell membrane, thereby providing the critical environment for living cells. The energy stored in the ionic concentration gradient is the source for many member proteins. For example, ion channels utilize the membrane potential to generate and propagate the action potential. Various secondary active transporters use the energy to actively transport sugars, amino acid, etc. From the viewpoint of a physicist, the Na/K pump is a unique energy converter converting ATP hydrolysis energy to the electrochemical potential difference across the cell membrane, so that the membrane proteins can easily use the energy.

Because Na/K pumps involve ion-transports across the cell membrane, they are sensitive to the membrane potential. In the last few decades, significant efforts have been made to electrically control or manipulate the pump functions. Previously, red blood cells have been studied and was found that a weak oscillating electric field, at a frequency of about 1.0 MHz and 1.0 KHz, can activate the Na- and K-transports, respectively. It was also found that an AC current can either stimulate or inhibit the ATP hydrolysis activity of enzymes, depending on the Na/K ratio. However, there are currently no practice techniques available that can effectively activate the Na/K pump functions while also conserving ATP molecules.

The energy generating synchronization modulation electric field, or the $3^{rd}$ generation synchronization modulation electric field, of the present invention is a practical technique that can effectively activate the function of Na/K pumps to develop the ionic concentration gradient and the membrane potential with less, or even zero, ATP-consumption. Moreover, the synchronization techniques were developed based on the dynamic model of the pump molecules. The successful synchronization modulation of the pumping rate and the substitution of ATP energy to fuel the pumping in the buildup of the ionic concentration gradients and the membrane potential support the dynamic model of the Na/K pumps as a microscopic machine.

FIG. 1A is an illustration representing the fundamental underlying mechanisms involved in the pump synchronization of the present invention. FIG. 1A illustrates four $Na^+/K^+$ pumps 100, 105, 110, 115 in the cell membrane 120. Pump molecules extrude $Na^+$ ions and pump in $K^+$ ions against their electrochemical potential differences, wherein all the pumps are naturally running at a random pumping pace.

Figure 1B:
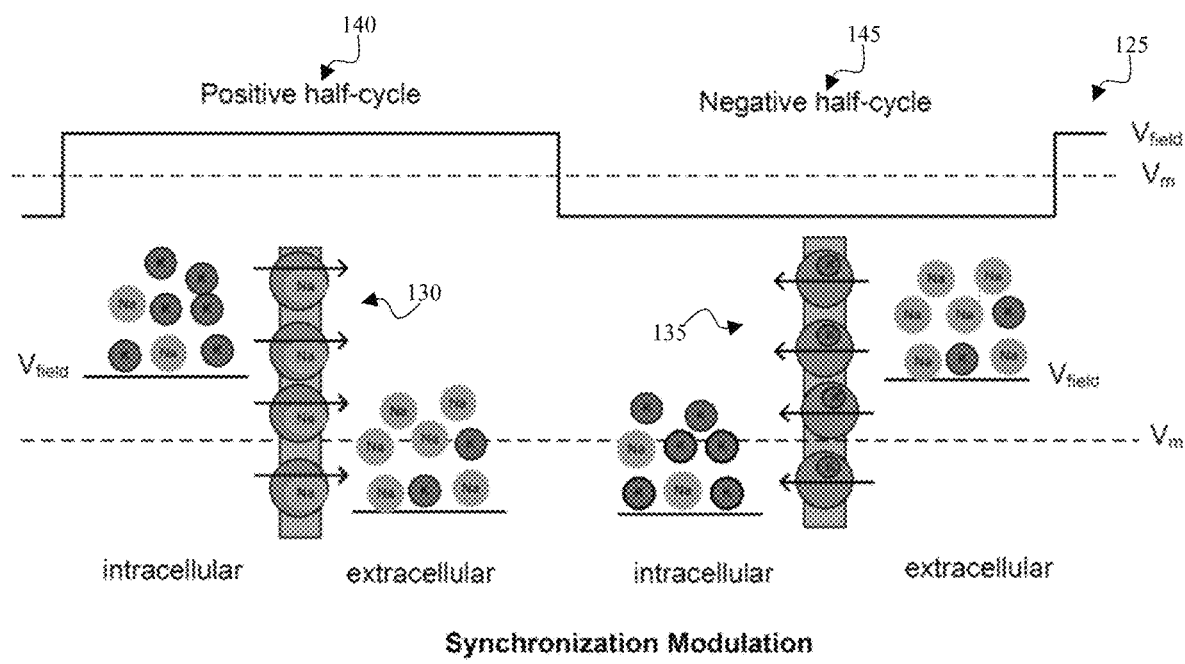
FIG. 1B illustrates synchronized pump molecules, in accordance with an embodiment of the present invention.

FIG. 1B illustrates the pumps 100, 105, 110, 115 synchronized by a pulsed, oscillating, electric field 125 with an oscillating frequency of 50 Hz, which is comparable to the natural turnover rate of the Na/K pumps. As the oscillating electric field 125 is applied to the cell membrane, Na-extrusion 130 and K-pumping in 135 from all the pump molecules are eventually entrapped into the positive half-cycle 140 and the negative half-cycle 145 of the oscillating electric field 125, respectively. The pumps simultaneously extrude 3 $Na^+$ ions during the positive half-cycle 140 and then pump in 2 K ions during the negative half-cycle 145. Once synchronized, the positive half-cycle 140 of the oscillating electric field 125 specifically affects the $Na^+$ extrusions while the negative half-cycle 145 affects the $K^+$ pumping in.

FIG. 1A illustrates a fundamental concept to utilize one electric field to handle a large amount of pump molecules, each running at random pumping pace and different pumping rates. The problem is that once the Na- and K-transports are entrapped into the positive and negative half-cycle of the oscillating electric field, the electric field will lose its control capability of the pump molecules. It is impossible to identify the specific position of the Na- and K-transports in the corresponding half-pulses. In addition, all these have to be in the presence of ATP molecules.

In the present invention, a $3^{rd}$ generation synchronization modulation electric field ($3^{rd}$ SMEF) was developed based on this concept. By special design of the oscillating electric field, it has been demonstrated that the outward movements of 3 Na ions and inward movement of 2 K ions across the cell membrane exhibits two separated, transient pump currents with extremely short duration of about 100 ms, which is shorter than any ion channel currents, including the voltage-gated Na channel currents (1 ms), which has the fastest electric response in living systems, and is similar to the membrane capacitance currents. The results indicate that Na and K ions are freely and mechanically moving across the cell membrane.

In addition, the specially designed $3^{rd}$ SMEF can synchronize the transient Na and K pump currents for all the pump molecules at the specific position in the corresponding positive and negative half cycle of the oscillating electric field. Based on physics law, these results imply that by appropriate design of the electric field, electric energy can be injected to the pump molecules by accurately and alternatively accelerating the Na and K ion-movements.

Furthermore, the $3^{rd}$ SMEF was designed to control the Na/K pumps molecules so that the pumps can, on one hand, actively extrude 3 Na ions and pumping in 2 K ions by consuming one ATP, and on the other hand, utilize the injected energy to synthesize one ATP in each pumping cycle. As a result, the synthesized ATP molecule compensates the ATP consumed in actively transporting Na and K ions. The net consumption of the ATP molecule of the Na/K pumps controlled by the electric field generated in accordance with the present invention is significantly reduced, theoretical to zero. As such, under the $3^{rd}$ SMEF, Na/K pumps run well in the non-physiological situations in sufficiency of the ATP supply.

Moreover, in the present invention, the $3^{rd}$ SMEF can modulate (accelerate or decelerate) the synchronized Na/K pumps running at different turnover rates by gradually changing, (increasing or decreasing) the synchronization frequency to a pre-determined value. As a result, in the present invention, the $3^{rd}$ SMEF can not only use electric energy to substitute ATP hydrolysis energy in fueling Na/K pumps in the non-physiological situation having a lack of ATP supply, such as the ischemia induced kidney injury, but can also activate or deactivate the pumping rate to satisfy the clinical requirements.

In the present invention, the $3^{rd}$ SMEF consists of three phases, Phase 1 is to synchronize the Na/K pumps down to the individual steps throughout the pumping cycle in actively transporting Na and K ions without ATP consumption. Phase 2 is to modulate the pumping rate of the synchronized pump molecules to a pre-determined target value. Phase 3 is to maintain the pumping rate at the target value for a certain period based on the clinical requirement.

Figure 2:
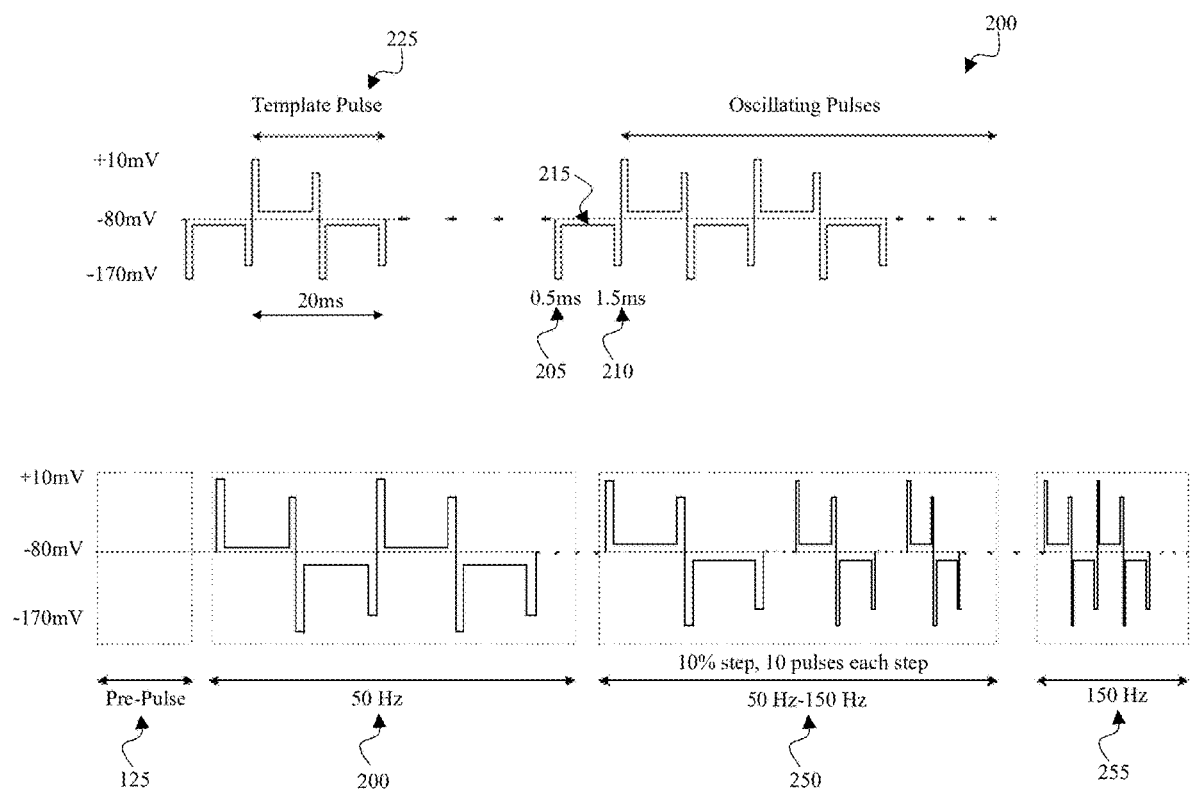
FIG. 2 illustrates the waveform of the present invention, the $3^{rd}$ generation synchronization modulation electric field.

FIG. 2 illustrates the waveform of the present invention, referred to herein as the $3^{rd}$ generation synchronization modulation electric field. In the synchronization phase 200, the electric field is a pulsed, symmetric, oscillating electric field consisting of two overshoot electric pulses in each half-cycle. First, is the activation overshoot electric pulse 205 with a duration of about 0.5 ms, or less, and a magnitude greater than about 90 mV followed by a plateau 215 of about 20 mV. Next, is the energy-trap overshoot electric pulse 210 having a duration of about 1.5 ms, or less, and a magnitude of about 70 mV.

It is noted that the magnitude of the electric field illustrated in FIG. 2 is applicable to the voltage-clamp experiments, or the potential difference across the cell membrane. For clinical applications, the applied field-strength should be adjusted to apply the proper electric field for the situation of the tissues and organs. The oscillating frequency is comparable to the natural turnover rate of the transporter used to synchronize the active ion transporters, or the Na/K pumps.

Also shown in FIG. 2 is a pre-pulse 225 that may be applied before the application of the oscillating electric field. The pre-pulse has the same waveform as the oscillating pulses. The pre-pulse 225 is used when the synchronized pump currents need to be identified. The currents generated by the pre-pulse 225 serve as the template to be subtracted from the currents generated by the individual oscillating pulses, with the resulting difference being the synchronized pump currents.

As such, the three phases of the oscillating electric field, in accordance with embodiments of the present invention, are illustrated in FIG. 2, wherein the pre-pulse 225 and the synchronization phase 200 are shown, as previously described, in addition to the modulation phase 250, where the oscillating frequency is gradually increased from about 50 Hz to about 150 Hz in a stepwise pattern, and the maintenance phase 255, where the field oscillating frequency remains at the target frequency.

In the modulation phase 250, the synchronization frequency or the frequency of the oscillating electric field will be gradually changed, going up or going down, to progressively modulate or entrain (accelerate or decelerate) the pump molecules to a pre-determined pumping rate. The waveform remains the same as that in the synchronization phase, and the oscillating frequency is gradually increased or decreased in a stepwise pattern (3% to 10% of the frequency change for 10 to 20 oscillating pulses) to a target frequency. By carefully maintaining the pump synchronization and gradually increasing or decreasing the synchronization frequency, the pump molecules can be entrained to higher and higher, or lower and lower, pumping rate, respectively, to reach a pre-determined value.

For the maintenance phase of the $3^{rd}$ SMEF, the frequency of the oscillating electric field is kept at the target frequency for a certain period of time, as determined by the specific requirement of the application. The waveform of the oscillating electric field remains unchanged.

For future applications, the $3^{rd}$-SMEF has been specifically designed to avoid side effects on the cell membrane. For example, to avoid changing the integrity of the cell membrane the field-induced membrane potentials are in physiological range, much lower than the thresholds of membrane electroporation and protein denature. The short duration of the overshoot pulses (a few hundred microseconds) is not long enough to open the voltage-gated ion channels, including the Na-channels having the fastest electric response, or effect other membrane proteins. The oscillating waveform of the $3^{rd}$-SMEF was specifically designed for Na/K pumps, transporting cations in the opposite direction, and the 50 Hz frequency is comparable to the turnover rate of Na/K pumps, which is far away from other pumps, such as Ca2+ pumps of 500 Hz.

In kidneys, the Na/K pump is highly expressed on the basolateral surface of tubular epithelial cells. The pump generated membrane potential across the basolateral membrane and the potential difference determines the transepithelial potential difference (TEPD). Due to ischemia, reduction of blood flow in the kidneys decreases the ATP concentration, which reduces the pump functions and therefore, the TEPD. The following experimental embodiment examines the effects of the energy generating synchronization modulation electric field on the proximal tubule epithelial cells in vivo by real-time monitoring of the changes in TEPD with micro-puncture technique. The effects of the energy generating synchronization modulation electric field on Na/K pump activity in normal (sufficient ATP) and ischemic (insufficient ATP) kidneys in vivo were examined in the following experimental embodiments.

Experiments were conducted on an isolated kidney separated from a rat, and within one hour after the isolation of the kidney from rat. The renal pedicle was clamped to avoid blood loss. In measuring the TEPD, a microelectrode with about 1 μm diameter was used to puncture into the lumen of proximal tubule to measure TEPD. The reference electrode was placed on the surface of the kidney. When the tip of the microelectrode enters into the epithelial cell, the measured potential suddenly reduces to about −50 mV. Continuously moving in, then the potential suddenly returns to a small value close to zero, which is the TEPD. Measurement of TEPD during kidney ischemia is used to examine if application of the energy generating synchronization modulation electric field maintains the pump function by substituting ATP molecules in fueling the pumping cycle during ischemia.

In the experimental procedures, the $3^{rd}$ forward synchronization modulation electric field ($3^{rd}$ forward SMEF) with a large frequency of 150 Hz was applied to the kidney by a pair of stainless-steel electrodes. The electrodes were placed on the kidneys so that the electric field was perpendicular to the proximal tubule. The energy generating synchronization modulation electric field was generated by a custom-made signal generator with a magnitude of about 200 mV.

Figure 3:
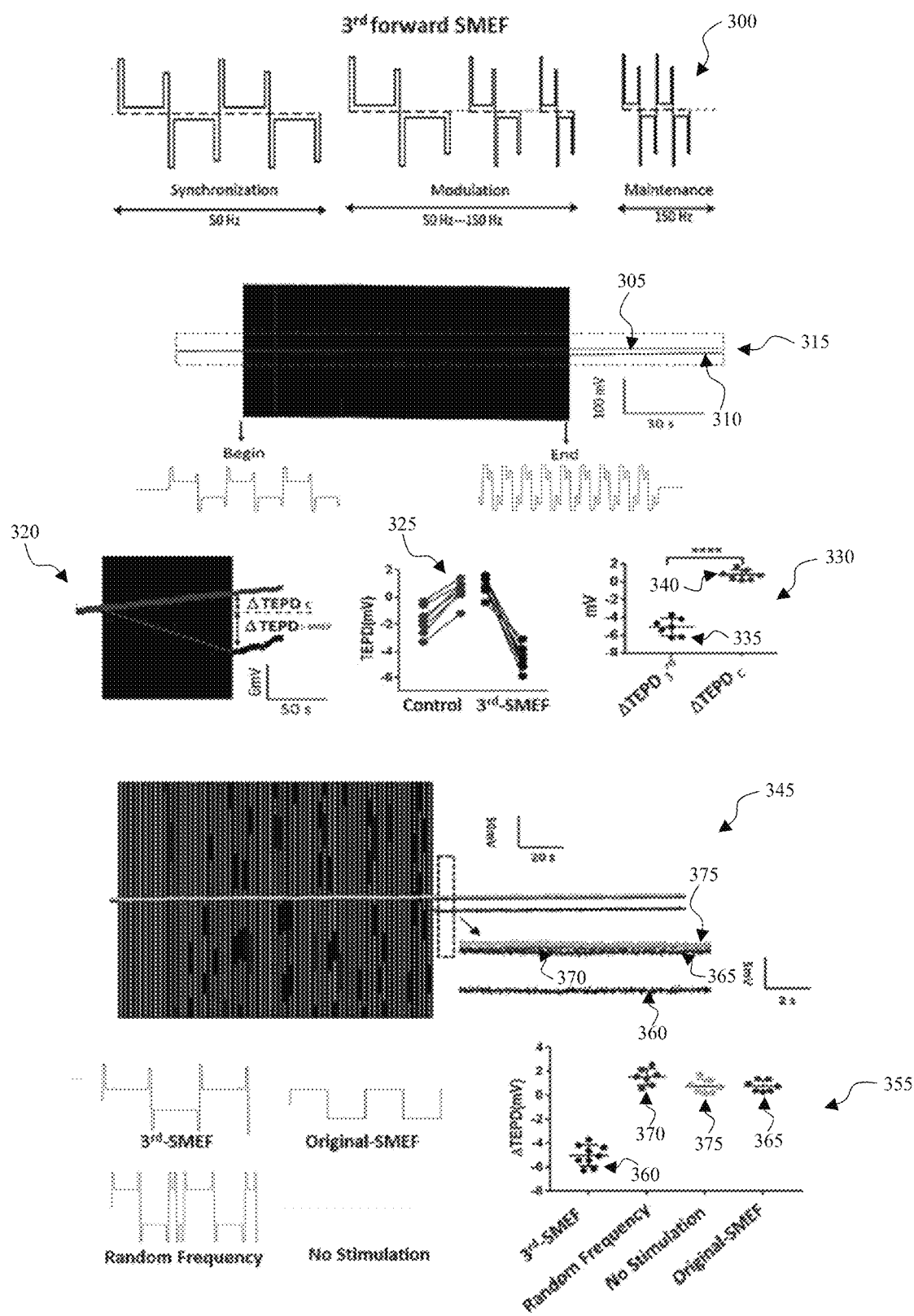
FIG. 3 illustrates the effects of the $3^{rd}$ forward synchronization modulation electric field on the Na/K pumps in maintenance of the transepithelial potential difference in the proximal tubule in ischemia treated kidney, in accordance with the present invention.

FIG. 3 shows the effects of the $3^{rd}$ forward SMEF on TEPD measured from the isolated kidney from rat, where the pedicle blood vessel was clamped to avoid bleeding. The experiments were conducted within one hour after the kidney was isolated from the rat, where the TEPD was measured by the micro-electrode technique. Illustration 300 shows the waveform of three phases for the $3^{rd}$ forward SMEF with the target frequency of 150 Hz. Due to clamping the pedicle blood vessel, ATP concentration in kidney is decreased resulting dysfunction of Na/K pumps.

As shown in illustration 315, as a result, TEPD was gradually decreased from −1 mV to 1 mV in about 120 s as a control 305. In contrast, application of the $3^{rd}$ forward SMEF increased the TEPD to −5 mV 310. The detailed changes are shown in illustration 320. Seven experiments were performed, as shown in illustration 325, and the statistic results for the TEPD changes are shown in illustration 330 for the control 335 and $3^{rd}$ forward SMEF 340. The $3^{rd}$ forward SMEF 340 not only maintains but also increases the TEPD to −5 mV, which is 6 mV difference from the control 335.

Illustration 345 compares the rescue effects from different electric fields 350 on the reduced TEPD, including the 3rd forward SMEF (360), 1st forward SMEF (365), random frequency (370), and no stimulation (375). TEPD changes measured in dashed-line box is enlarged and shown as the insert. As shown in the insert of illustration 345, only the 3rd forward SMEF (360) increased the TEPD. Illustration 355 is the statistic result of ATEPD from seven experiments. The long bars are the mean values. As shown in illustration 355, only the 3rd forward SMEF increased the TEPD to about −5 mV. The results proved that the 3rd forward SMEF is capable of maintaining, or even increasing the TEPD, to rescue the epithelial cells from the ischemia injury.

The field induced changes in TEPD indicate that the in present invention, the $3^{rd}$ generation synchronization modulation electric field not only can be applied in vivo to whole kidney, but also can facilitate the functions of Na/K pumps to maintain the TEPD.

Figure 4:
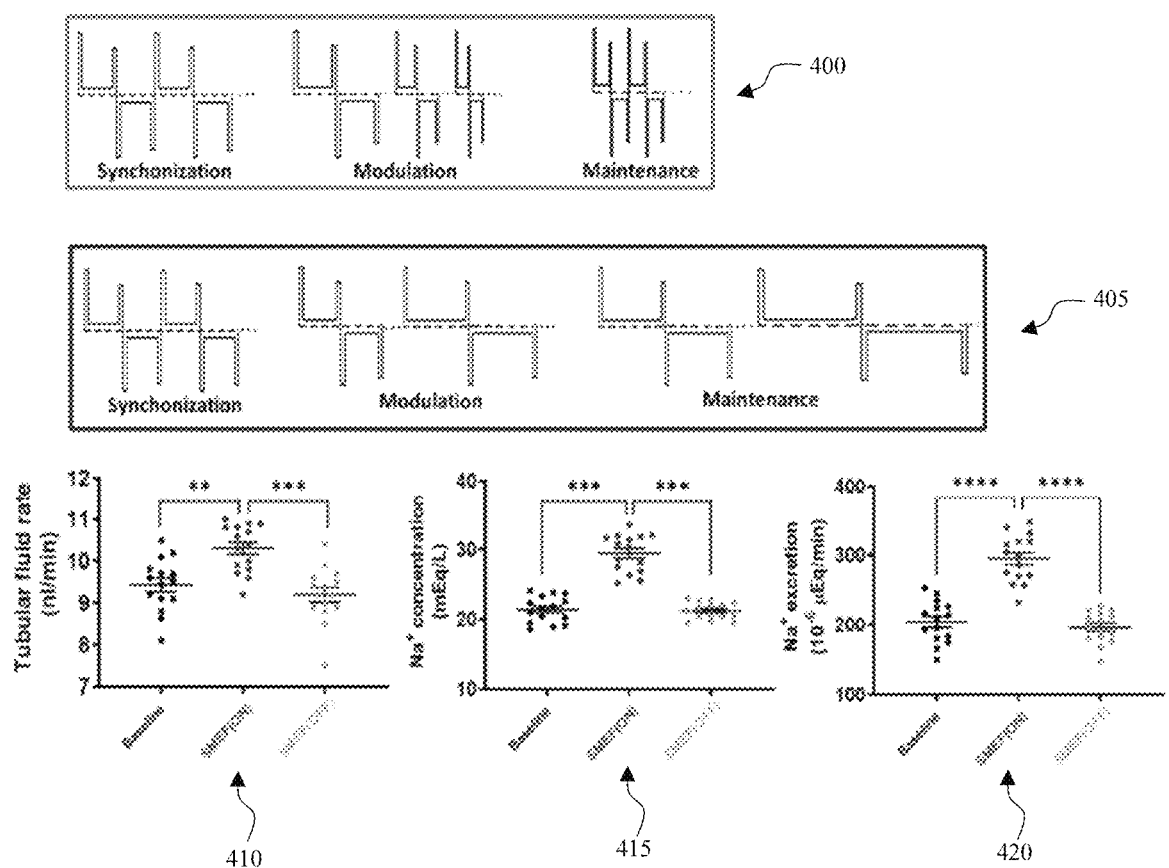
FIG. 4 illustrates the effects of the $3^{rd}$ synchronization modulation electric field on the tubular fluid rate, Na concentration and Na excretion, in accordance with embodiments of the present invention, measured in the tubular level.
Figure 5:
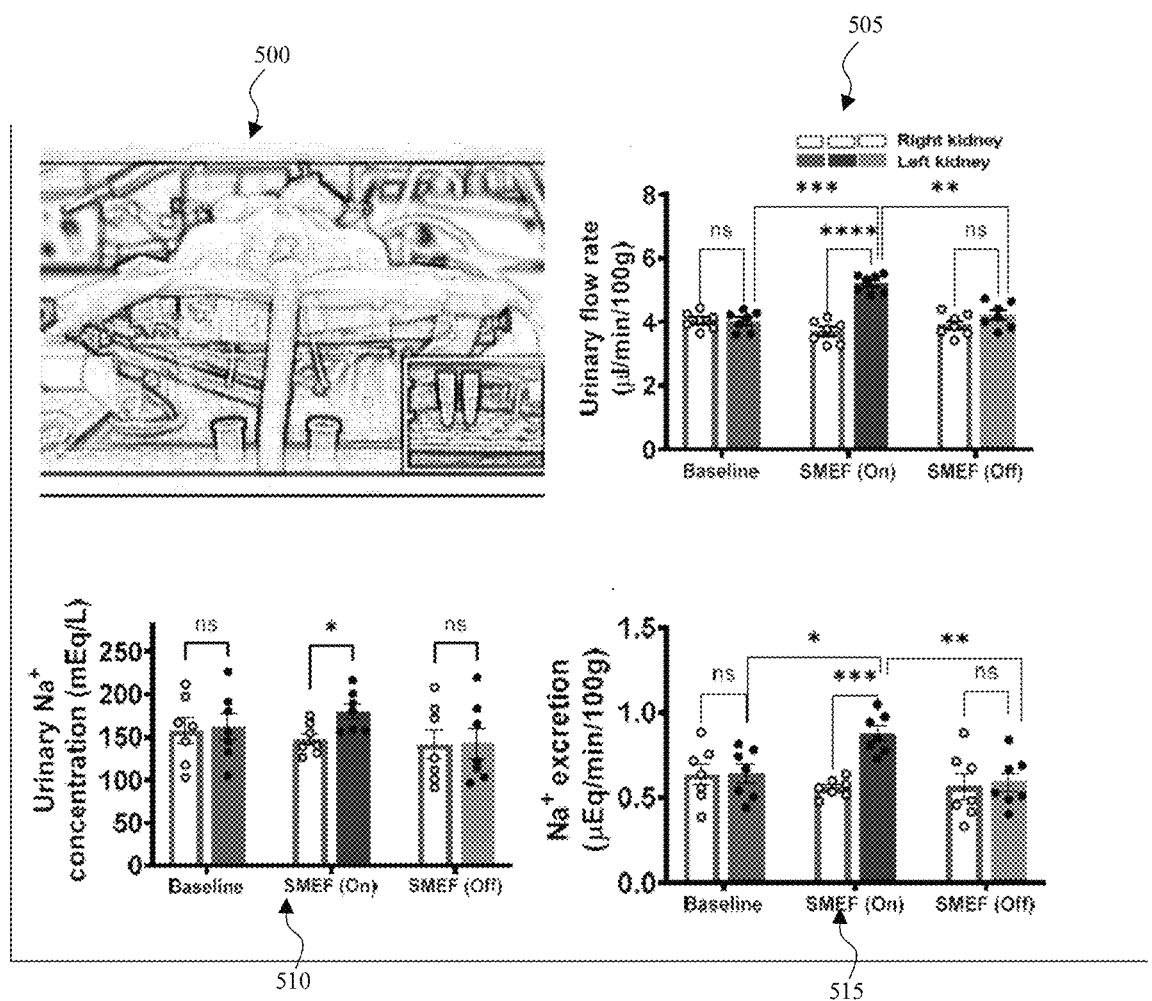
FIG. 5 illustrates the effects of the present invention, the $3^{rd}$ generation synchronization modulation electric field on the urinary flow rate, urinary Na concentration, and Na excretion in kidney level, in accordance with embodiments of the present invention.

FIG. 4 and FIG. 5 illustrate the effects of the $3^{rd}$ forward SMEF of the present invention, in the regulation of saltwater and blood pressure in healthy animals to determine if the $3^{rd}$-SMEF can be effectively applied to the whole kidney and affect tubular functions by controlling (increasing or decreasing) the Na/K pump activities in vivo, urinary and Na excretion rates were measured in the single tubular levels (FIG. 4) and in the whole kidneys (FIG. 5) in vivo, in response to backward modulation of the 3rd-SMEF on Sprague Dawley (SD) kidneys.

For regulation of the present invention, the $3^{rd}$ backward SMEF on tubular flow and Na+ excretion at a single tubular level were measured. Tubular flow and $Na^+$ excretion rates were measured with micro-puncture. Animal preparation has been previously described in the method section of previous reports. Tubular fluid rates, Na+ concentration, and Na+ excretion rates were measured before, during, and after the application of the 3rd-SMEF. When the $3^{rd}$ backward SMEF was turned on (from 50 to 10 Hz to decrease Na+/K+ pumping activities), $Na^+$ concentrations and $Na^+$ excretion rates at early distal tubules were significantly increased by 45%. When the $3^{rd}$ backward SMEF was turned off, Na+ concentrations and Na+ excretion rates returned to baseline quickly (FIG. 4, n=15 tubules in 3 rats). This data provides supportive evidence for the $3^{rd}$ backward SMEF induced regulations of tubular Na+ reabsorption from single tubular levels.

Illustration 400 of FIG. 4 shows the forward modulation of 3rd-SMEF to increase the Na+/K+ pumping activities. Illustration 405 of FIG. 4 is the backward modulation of the 3rd-SMEF to decrease Na+/K+ pumping activities.

Illustration 410 of FIG. 4 shows the tubular flow rates, illustration 415 of FIG. 4 is the tubular Na+ concentrations and illustration 420 of FIG. 4 shows Na+ excretion rates. All the results were measured with micro-puncture at the early distal tubule in anesthetized SD rats. The tubular fluid was collected by glass micropipettes with a diameter of 8 μm for 30 minutes before (baseline), during (SMEF on) and after (SMEF off) application of the $3^{rd}$ generation backward synchronization modulation electric field (from 50 to 10 Hz), respectively. Because the backward modulation electric field decelerated Na/K pump activities, Na concentrations shown in illustration 415 and Na+ excretion rates shown in illustration 420 were significantly increased by 45%. When the 3$^{rd}$ backward SMEF was turned off, Na concentration and Na excretion rates returned to baseline. Repeated-measures ANOVA was performed (Asterisks represent an analysis with Tukey's multiple comparison test, *P<0.01; *P<0.001; **P<0.0001, n=15 tubules in 3 rats, Data are presented as mean±s.e.m.)

Urinary flow rates, urinary Na+ concentrations and Na+ excretion rates of kidney are directly related to the functioning of the Na/K pumps. The effects of the 3$^{rd}$ SMEF on the Na/K pumps should be reflected on the control of the urinary flow rate, Na concentration in urine and Na excretion rate. In this group of experiments, urinary flow rates, urinary Na concentrations and Na excretion rates from both kidneys in SD rats were measured with left kidney of the rat applied with 3$^{rd}$ backward SMEF (target frequency of 10 Hz) for 30 minutes and the right kidney of the rat without the field application, as a control.

The urine was collected into Eppendorf tubes with PE-50 tubing cannulated to the ureters, as shown in illustration 500 of FIG. 5. The collection was carried out for 30 minutes before (baseline), during (SMEF on) and after (SMEF off) the field application. Then, the urinary flow rate, Na concentrations, and Na excretion rates were tested, respectively. Urinary flow and Na excretion was measured from urine collected with metabolic cages and with a Flame Photometer.

The results of urinary flow rates, urinary Na concentration, and urinary Na excretion rates are shown in illustration 505, 510 and 515 of FIG. 5, respectively. During the 30-minute equilibrium period, left and right kidneys had the similarly basal urinary flow and Na excretion rates. After the 3$^{rd}$ backward SMEF was turned ON in the experimental kidney, the urinary volume shown in illustration 505 was 554 µl from left kidney and 392 µl from right kidney at the end of 30 min-stimulation. The urinary flow rates and the Na excretion rates were increased by 40% and 50%, respectively, while there were no changes in the control kidney.

In the represented experiment illustration of FIG. 5, once the synchronization modulation electric field was applied, the urinary flow rate of the left kidney was immediately increased compared to the right kidney (without the field application). More specifically, the flow rate of the left kidney increased to 5.6±0.3 µl/min/100 g BW as shown in illustration 505 accompanied with an increased Na excretion rate to 0.8+0.2 mEq/min/100 g as shown in illustration 515. Once the electric field was turned OFF, all the measured parameter values returned to the levels similar to the baseline. Repeated measures ANOVA was performed (Asterisks represent an analysis with Bonferroni's multiple comparison test, n=7 rats, *p<0.1 P<0.01; *P<0.001; ****P<0.0001; Data are shown as mean±s.e.m)

These results showed that the 3$^{rd}$ backward SMEF decreased pump activities and blunted sodium and water reabsorption reflected by the significantly increased urinary flow rates and the Na excretion.

Figure 6A:
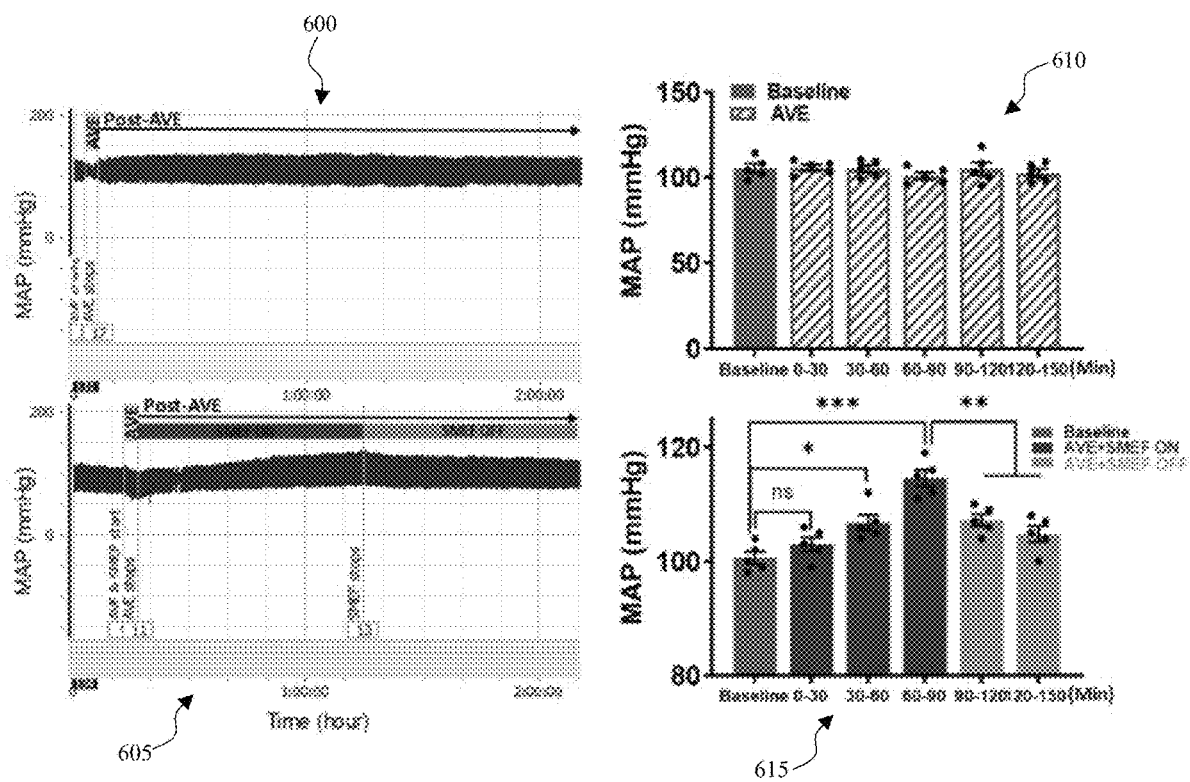
FIG. 6A illustrates results of the present invention, the $3^{rd}$-SMEF in regulation of Na+ and urinary excretion and blood pressure following acute volume expansion (AVE).

FIG. 6A and FIG. 5B illustrate results of the 3$^{rd}$ SMEF regulated Na and urinary excretion and blood pressure in response to acute volume expansion (AVE). In this experiment, the 3$^{rd}$ forward SMEF was applied to the kidneys and the urinary and Na excretion rate and blood pressure in response to AVE were measured. The mean arterial pressures (MAP) were measured throughout the experiment. The urine samples (from both ureter catheters) collected continuously for 30 minutes before AVE were taken as the baseline. Then the rats were given an AVE. For the experimental group, the 3$^{rd}$ forward SMEF (from 50 Hz to 150 Hz) was simultaneously turned ON. Urine samples were collected at 30 min intervals after AVE. Then, the 3$^{rd}$ forward SMEF was turned OFF at 75 minutes after AVE. The urine samples were collected for additional 1 hour.

Illustrations 600 and 605 of FIG. 6 illustrate the representative experiments of MAP levels following AVE with 605 and without 600 the 3$^{rd}$ forward SMEF application. As shown in illustration 600, MAP was stable following AVE in the control group. As shown in illustration 605, MAP slowly increased by 14 mmHg at 75 min in response to the 3$^{rd}$ forward SMEF application following AVE in experimental group. When the 3$^{rd}$ forward SMEF was turned OFF, the MAP gradually decreased and returned to baseline. Illustrations 610 and 615 of FIG. 6 illustrate the averaged MAP following AVE without, or with, the 3$^{rd}$ forward SMEF application, respectively.

Figure 6B:
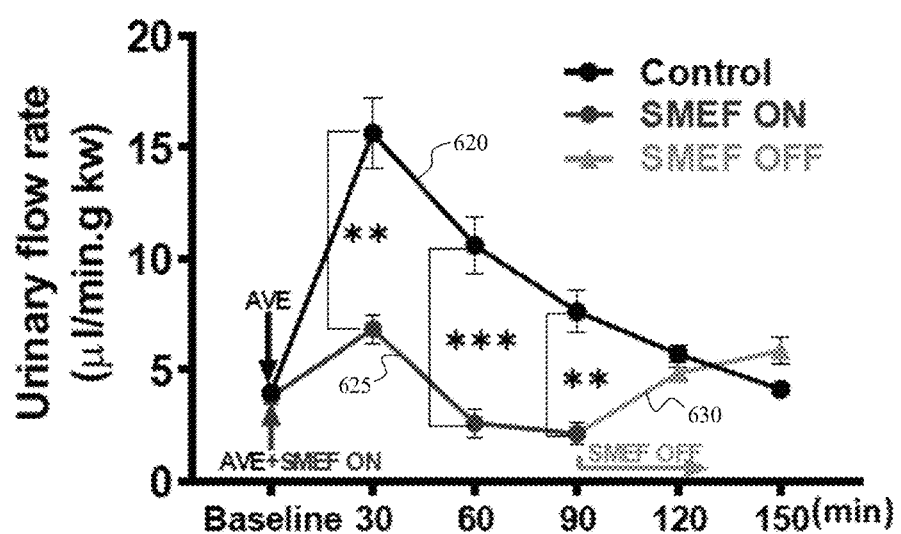
FIG. 6B illustrating a graph of the urinary flow rate related to the $3^{rd}$-SMEF in regulation of Na+ and urinary excretion.

FIG. 6B shows the urinary flow rate response to the stimulation of the 3$^{rd}$ forward SMEF, following AVE. The control 620 reflects the changes of urinary flow rate for the control groups and curve 625 reflects the respective changes for the experimental groups. The dots on curve 625 represent the time points measured when the 3$^{rd}$ forward SMEF was ON and the dots on curve 630 are for the time points measured when the 3$^{rd}$ forward SMEF was OFF. The urinary flow rates measured when the 3$^{rd}$ forward SMEF was ON were compared to the control group by unpaired t-test (P<0.01; *P<0.001; ****P<0.0001; n=5/group; Data are presented as mean±s.e.m).

As shown in FIG. 6B, the basal urinary flow rates for the control and experimental group were similar, which was about 4.03±0.3 µl/min/g KW. Following the AVE, the urinary flow rates of the control group started to increase and reached the maximum of 4-fold increase over baseline in 30 min after AVE, while the MAP was stable during the whole experimental period, as shown in illustration 600. In the experimental group, the 3$^{rd}$ forward SMEF (from 50 HZ to 150 HZ) significantly blunted the increase of the urinary flow rates in response to AVE, as shown by 625 in FIG. 6B. Consequently, the MAP gradually increased by 14 mmHg at 75 min after AVE, as shown in illustrations 605 and 615. When the 3$^{rd}$ SMEF was turned OFF at 75 min after AVE, urine flow rate increased, as shown by curve 630 of FIG. 6B, and correspondingly the MAP gradually decreased to the baseline value.

This data demonstrates that the 3$^{rd}$ forward SMEF can effectively regulate urinary excretion and blood pressure following AVE.

To examine if the 3$^{rd}$ SMEF can be effectively applied on conscious animals, hypertension was induced in SD rats by chronic infusion of sub pressor dose of Ang II (200 ng/kg/min) with mini-osmotic pumps and the effect of the 3$^{rd}$ backward SMEF on the blood pressure regulation was tested. During the surgery, each kidney was wrapped up with two pairs of electrodes having the alternative polarity touching on the kidney surface. The electrodes were connected to the device to apply the 3$^{rd}$ backward SMEF (from 50 Hz to 20 Hz). Then, both kidneys were put back into the rats, and the abdominal incision was closed, and the mice were allowed to recover. The MAP was monitored with radio-telemetry system.

Figure 7:
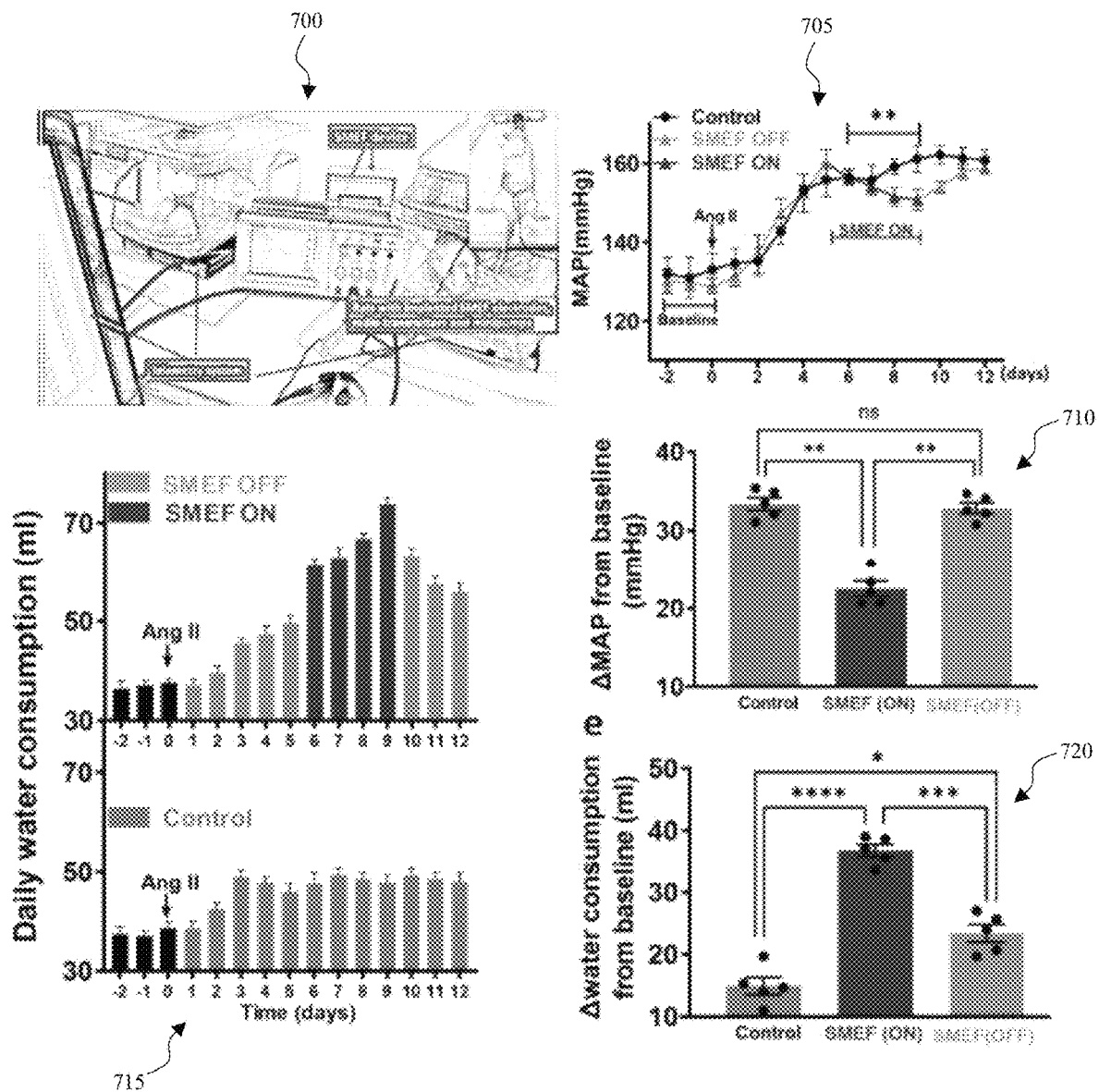
FIG. 7 illustrates the effects of the 3rd-SMEF on the blood pressure regulation, where hypertension in SD rats by chronic infusion of subpressor dose of Ang II, and the MAP was monitored with radio-telemetry system.

Illustration 700 of FIG. 7 is a representative photo for the experimental set-up, illustration 705 of FIG. 7 is the MAP measurement by telemetry system, illustration 710 FIG. 7 shows the increase in MAP from baseline, illustration 715 of FIG. 7 shows daily water consumption and illustration 720 of FIG. 7 represents the changes of water consumption in response to Ang II or 3$^{rd}$ SMEF.

As shown in illustration 705, MAP in the control group 725 gradually elevated and reached a plateau in about a week of Ang II infusion. The MAP started to increase at 2-3 days after Ang II infusion and gradually reached a plateau with an increase of about 30 mmHg at 6-8 days after Ang II infusion. Daily water intake was about 36±2 ml at baseline and 44±3 ml during Ang II infusion, as shown in illustration 715.

As shown in illustration 705, in the experimental rats application of the $3^{rd}$ backward SMEF from the 6th day of Ang II infusion and keeping it ON for 4 days (6th-9th days, red curve) lowered MAP by 8 mmHg. The increases in MAP from baseline accompanied by increased water consumption by about 13 ml/day, about 30% vs control (indicating increased excretion of water and possible Na), as shown in illustrations 705, 710, 715, 720. (Repeated measures ANOVA followed by Tukey multiple comparisons test, P<0.01; *P<0.001; ****P<0.0001). When the $3^{rd}$ backward SMEF was then turned OFF at 10th days of Ang II infusion, MAP and water intake returned to the similar levels of the controls in 2-3 days (n=5, Data are presented as mean±s.e.m).

This data demonstrates that the $3^{rd}$ backward SMEF can be efficiently applied in conscious animals to reduce the Ang II-induced hypertension, possibly by promoting Na and water excretion.

In a particular embodiment, the method of controlling an active ion transporter can be applied to reduce ischemia during kidney procurement and transplantation. Ischemia and ischemia reperfusion injury (IRI) are unavoidable steps during kidney procurement and transplantation. Transplanted organs experience several episodes of ischemia and IRI, which can be caused by both warm and cold ischemia. Warm ischemia occurs after cardiac death in donors, or during the harvest operation on living donors, and during anastomosis of the graft. Cold ischemia occurs during allograft kidney storage in preservation solutions. Post-transplant renal injury has been studied extensively. Prolonged ischemia of donor grafts increases the occurrence of delayed graft function and worsens long-term graft survival. IRI is one of the most important nonspecific factors affecting both early and late allograft dysfunction. RIFLE (risk, injury, failure, loss, end-stage renal disease) and Acute Kidney Injury Network (AKIN) criteria are commonly accepted definitions of an AKI episode in native kidneys, which are largely based on the degrees of plasma creatinine elevation from baseline. There are no official recommendations regarding specific diagnostic criteria for AKI in the kidney transplant, primarily due to the difficulties in determining baseline creatinine levels in graft recipients. The few published studies of transplant AKI epidemiology and outcomes have adopted the criteria for native kidneys. IRI-induced AKI has been found crucial for transplanted kidney survival. A recent large retrospective cohort study analyzed AKI and graft survival in 27,232 renal transplant recipients. Patients who developed AKI had a significantly increased risk of graft loss and mortality.

In the preliminary studies, it has been demonstrated that the $3^{rd}$ generation synchronization modulation electric field of the present invention is effective in maintaining Na/K pump activity in the absence of ATP in vitro, as well as protecting against IRI in AKI and KTX models in vivo. Additionally, application of the novel electric field was shown to ameliorate tubular injury in human kidneys.

An exemplary experimental analysis for protecting against IRI in kidney procurement and transplantation in accordance with the methods of the present invention is described in the following paragraphs.

The animals and experimental groups include male and female C57BL/6 mice. The animals were randomly divided into three groups: 1) For the IRI procedure, mice underwent the same procedures and time course as the IRI, but without clamping the renal pedicle to serve as sham controls. 2) Untreated IRI control: electrodes were placed in the same way as in the field application group, except no electric field was applied. 3) the $3^{rd}$ forward SMEF treated-IRI group. The administration of the synchronization modulation electric field was performed in a double blinded manner, both the surgeon and the person who operated the energy generating synchronization modulation electric field had different coding systems for the animals. All data presented in the preliminary studies are expressed by mean±SEM, unless otherwise stated.

The IRI and AKI were performed as follows. Briefly, the C57BL6 mice were anesthetized with pentobarbital (50 mg/kg i.p.). A middle abdominal incision was made, the left renal artery was identified and separated from the surrounding tissue. The left renal pedicle and left kidney were exposed and separated from the surrounding tissue, which is the experimental kidney to be applied with or without the electric field. The renal pedicle was clamped using microvascular clamps for 20 min with the body temperature at 37° C., respectively. The electric field was applied during clamping. Immediately following the release of the clip, the right kidney was nephrectomized, the abdominal incision was closed, and the mice were allowed to recover. Renal function and injury markers were measured at 1, 3, and 7 days after IRI.

Figure 8:
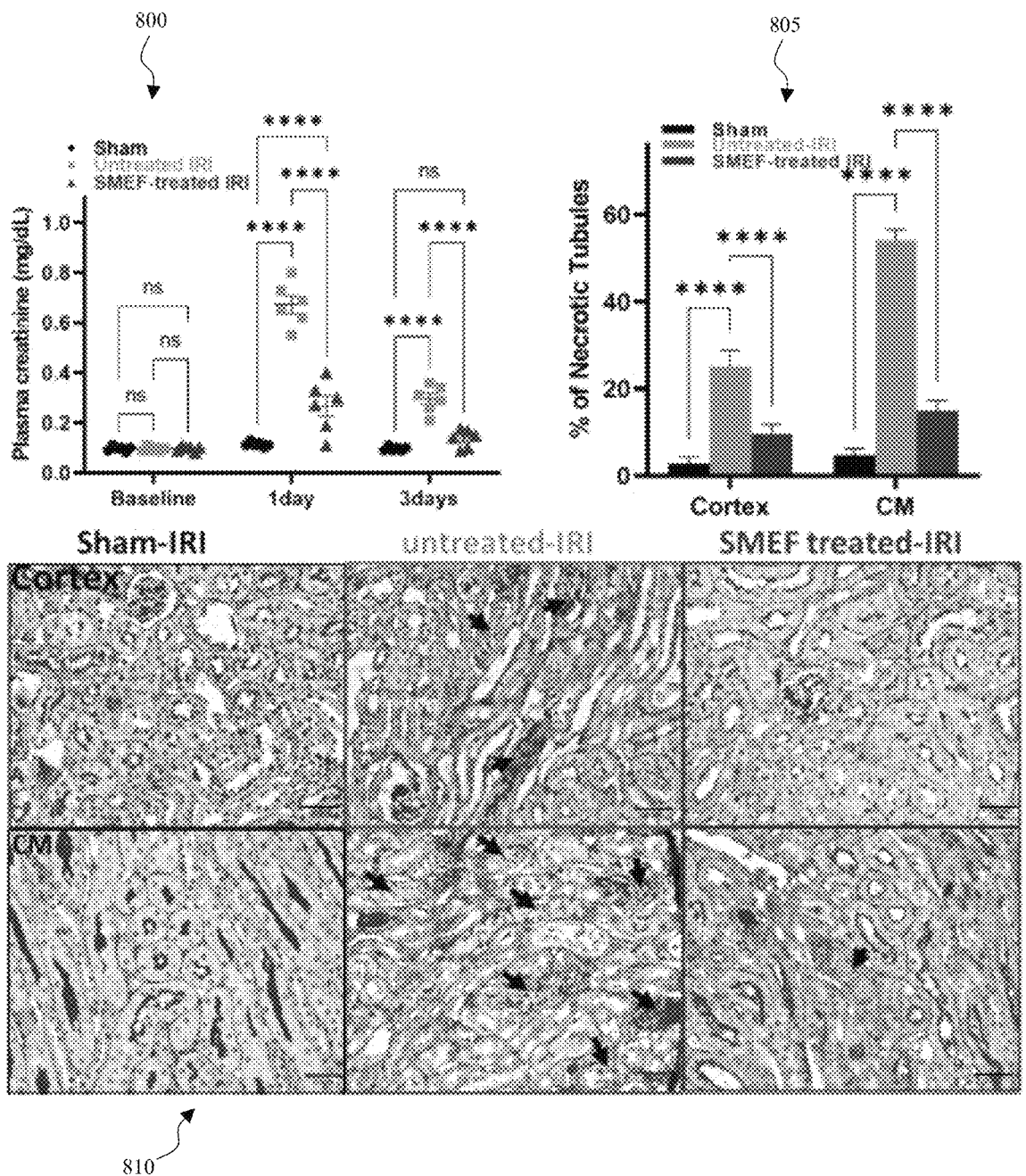
FIG. 8 illustrates the protective effect of the 3rd-SMEF in ATP deficient or depleted conditions, in the IRI-AKI and KTX mouse models.

Illustration 800 of FIG. 8 illustrates Plasma creatinine (Pcr) levels before (baseline) and at 1 or 3 days after reperfusion. Pcr was measured with a high-performance liquid chromatography (HPLC) method at the O'Brien Center in University of Alabama at Birmingham (UAB). Illustration 805 of FIG. 8 shows the percentage of the tubular necrosis based on the histology analysis. ANOVA followed by Tukey multiple comparisons test have been performed (****P<0.0001, n=6, data are presented as mean±s.e.m).c, PAS staining (CM, cortical medulla).

The kidney injury levels were evaluated at days 1 and 3 after reperfusion. As shown in illustration 800, the basal values of Pcr for all three groups were similar at about 0.1±0.01 mg/dl. At day 1, Pcr significantly increased to 0.67±0.05 for the untreated control group, while only a slight increase to 0.27±0.06 mg/dl in the $3^{rd}$ forward SMEF-treated group, which is only about 40% for the untreated control group. At day 3, Pcr reduced to 0.30±0.03 and 0.15±0.02 mg/dl for the untreated and the $3^{rd}$ forward SMEF-treated groups, respectively, about 50%.

Histology, as shown in illustrations 805 and 810 of FIG. 8, exhibited the tubular injury and necrosis in both cortical and cortical-medullary (CM) regions. From the PAS staining sections, the $3^{rd}$ SMEF treated group showed about 64% and 70% less necrotic tubules than the untreated group, for Cortex and CM. The black arrows identify the necrotic tubules. Both the Pcr levels and the PAS analysis demonstrated that $3^{rd}$ forward SMEF treatment during the ischemia significantly protected the kidney from ischemia induced injury (n=6, p<0.001, one-way Anova, Tukey). The $3^{rd}$ forward SMEF treated group exhibited significantly less tubular injury than the untreated control group. The results demonstrated that the application of $3^{rd}$ forward SMEF during ischemia greatly alleviated the kidney injury in IRI-AKI mice.

The protective effects of present invention were further tested, by applying the $3^{rd}$ SMEF on the donor kidney graft during cold storage to improve the graft functions in a mouse kidney transplantation model and in human renal allografts. To determine whether the present invention, the $3^{rd}$ generation synchronization modulation technique improves transplanted kidney function by reduction of IRI via maintaining the Na/K pump functions during ischemia, the $3^{rd}$ generation synchronization modulation electric field was tested in two animal models, including, IRI-induced AKI by clamping of renal pedicles and kidney transplantation in mice, wherein kidney injury markers and renal functions are measured. In addition, this technique was tested in discarded human donor kidneys. Kidney injury was evaluated with histology in light and electron microscopy and tubular injury markers.

KTX was performed in mice between same sexes. Briefly, donor C57BL/6 mice were anesthetized with isoflurane, a midline abdominal incision was made to fully expose the left kidney, aorta and inferior vena cava (IVC), the kidney and associated vessels were completely isolated, and the kidney was stored in 4° C. cold saline with or without the $3^{rd}$ generation forward synchronization modulation electric field application (from 50 Hz to 150 Hz) for 1 or 2 hours. The application of the electric field to the kidney was the same as in the IRI-AKI model described above. Recipient C57BL/6 mice were anesthetized with isoflurane, a midline abdominal incision was made, the aorta and vena cava inferior to the renal artery and vein were fully dissected and a section of aorta and IVC was cross-clamped and cut. Then, the donor kidney implantation was performed. The donor kidney was transferred to the right flank of the recipient mouse. The arterial and venous anastomosis was performed in an end-to-side manner with 10-0 Ethilon sutures. After that, the clamps were released sequentially for reperfusion of the transplanted kidney. The ureter was fixed to the exterior wall of the bladder dome using a 10-0 Ethilon suture. Then, the remaining contralateral native kidney was removed. Finally, the abdomen was closed, and the animal was allowed to recover.

At days 5 and 8 after the transplantation, Pcr level was measured. As shown in illustration 900 of FIG. 9, Pcr was significantly increased to 0.72±0.04 and 0.43±0.04 mg/dl at days 5 and 8, respectively, post-KTX for the untreated group. However, for the $3^{rd}$ forward SMEF-treated groups, the Pcr increased to only 0.43±0.04 and 0.24±0.03 mg/dl at days 5 and 8 after KTX, respectively. Pers were lower by 40% and 20% in the $3^{rd}$-SMEF treated mice than untreated mice. Pcr did not change significantly for the sham-operated mice through the study period. Glomerular filtration rate (GFR) was measured in conscious recipients at day 11 post-KTX. The $3^{rd}$ forward SMEF-treated group exhibited about 50% higher in GFR than the untreated group, as shown in illustration 905 of FIG. 9, (n=5 mice/group, *p<0.05 vs baseline). The results demonstrated that the $3^{rd}$ forward SMEF protected the donor kidneys and improved the transplanted graft function.

GFR was measured in conscious recipients, as described above, at 11 days post-KTX. GFR was measured in conscious mice with a single bolus injection of FITC-sinistrin (5.6 mg/100 g body weight) via the retro-orbital sinus. Blood (<5 μL/sample) was collected into heparinized capillary tubes by the tail vein at 3, 7, 10, 15, 35, 55, 75, and 90 minutes after injection. GFR was calculated with GraphPad Prism based on the FITC-sinistrin fluorescence of the plasma samples (2 μL/sample), which was measured by a plate reader. The $3^{rd}$ forward synchronization modulation electric field treated group exhibited about 50% higher in GFR than untreated group, indicating better graft function than untreated group (n=5 mice/group, *<0.02 vs other groups; #, p<0.05 vs baseline). ANOVA followed by Tukey's multiple comparison tests have been performed (P<0.01; **P<0.0001; n=5 mice/group; Data are shown as mean±s.e.m).

Figure 9:
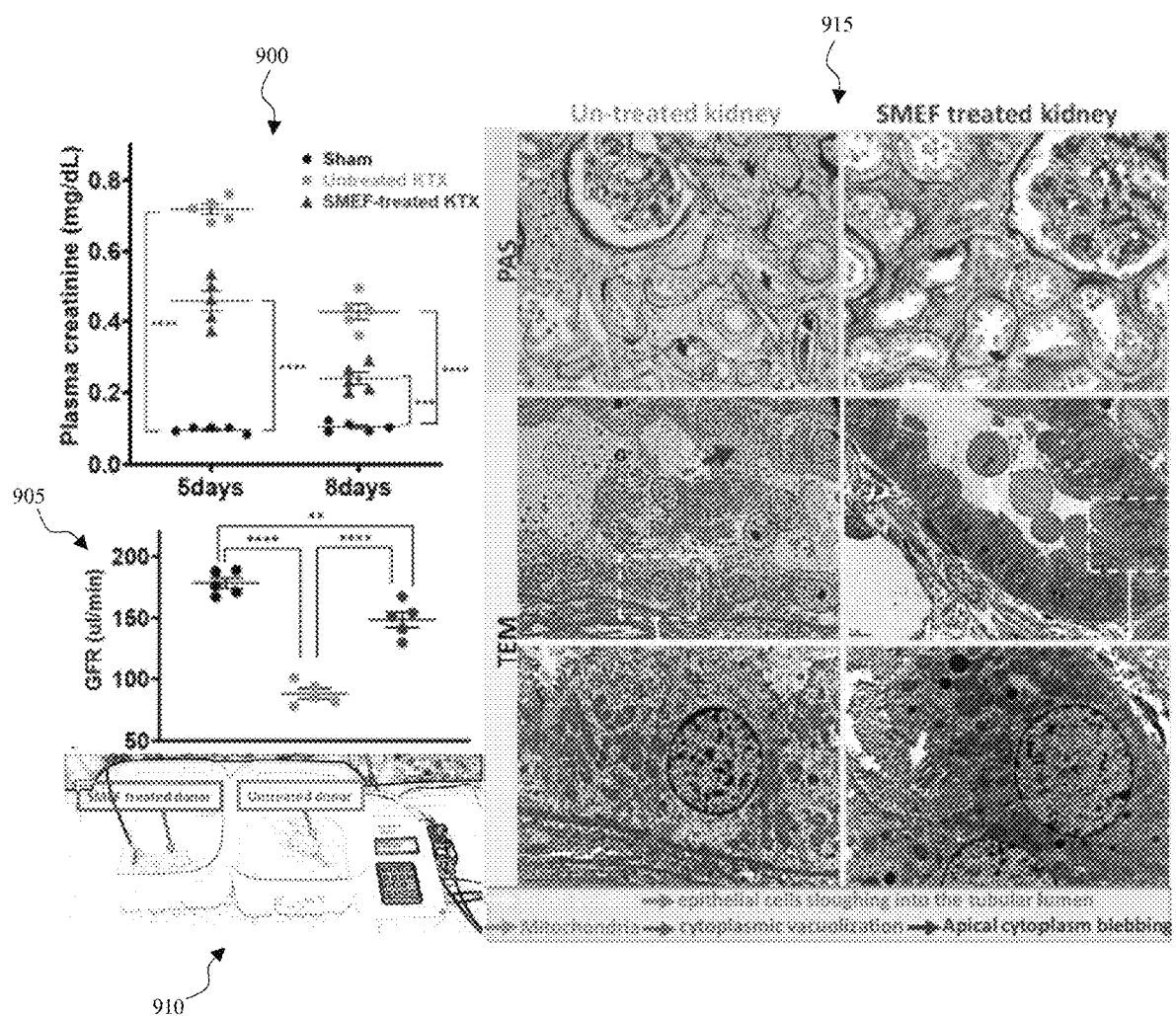
FIG. 9 illustrates the protective effect of present invention, the 3rd-SMEF on the donor kidney graft during cold storage to improve the graft functions in a mouse kidney transplantation model and in human renal allografts.

To investigate the potential translational application of the present invention, the $3^{rd}$ SMEF technique was tested in human renal allografts from organ donors. For human kidney donors who are not viable for transplant and discarded, access to these organs was requested from Tampa General Hospital for experimental research. Once a pair of donor kidneys has been received, one kidney will be stored in University of Wisconsin (UW) cold storage solution as the untreated control and another kidney from the same donor will be applied with the present invention, the $3^{rd}$ forward SMEF (1.5V-0.6V-1.2V, and the target frequency of 150 Hz) during the subsequent storage for 24 hours. After that, the kidney tissue was collected to evaluate histological changes and tissue injury. Illustration 910 of FIG. 9 is a representative image for the application of $3^{rd}$-SMEF on discarded human donor kidneys. The pair of the control and treated kidneys were from the same kidney donors (n=5 pairs of kidney grafts from 5 kidney donors).

Histology was used to assess the morphological changes. Formalin-fixed kidney tissues were embedded in paraffin and 4 μm kidney tissue slices were serially cut. The slices were stained with Periodic Acid Schiff (PAS) or trichrome for assessment of kidney injury or fibrosis, respectively. Ten randomly chosen fields were captured under 200× magnification from the cortex, corticomedullary region and outer medulla. The degree of injury and fibrosis was determined and quantified in each image. All morphometric analyses were performed in a blinded manner and mortality was recorded. Top two images in illustration 915 of FIG. 9 are the results of histological analysis of human kidney slices stained by PAS. Red arrows indicate the loss of brush borders, cytoplasmic vacuolization and nuclear drop out. The untreated control group exhibited more severe tubular injury than the treated group.

Lower 4 panels of illustration 915 are Transmission Electron Microscopy (TEM) image, which was performed to examine the ultra-structural changes on the renal graft tissues after 24 hours storage in UW solution. To perform TEM, the kidney tissue was cut into about 1 mm³ pieces and fixed in 2% glutaraldehyde in 0.1 M sodium cacodylate buffer overnight. Then the kidney tissues were treated with 1% osmium tetroxide, dehydrated with a series of graded ethanol, sequentially infiltrated with 2:1, 1:1, and 1:2 mixtures of acetone and resin, and embedded in 100% resin. Thin sections (approximately 90-100 nm) were cut and examined with the transmission electron microscope (JEM-1400Plus). The average tubular atrophy and acute tubular epithelial cell injury were measured as described.

The $3^{rd}$ forward SMEF treated kidneys showed more preserved histological structures than untreated kidneys. The untreated kidney showed more severe tubule injuries as loss of brush borders, apical blebbing, cytosolic vacuolization of the epithelial cells, as well as detachment and sloughing of the epithelial cells from basement membranes (Yellow arrows, brush border; green arrows, epithelial cells sloughing into tubular lumen; blue arrows, mitochondria; brown arrows, cytoplasmic vacuolization and pink arrows, apical cytoplasm blebbing). The untreated kidney tissue also exhibited increased elongated and lysed mitochondria. The $3^{rd}$ forward SMEF-treated kidney tissue showed relatively intact epithelial cells with preserved brush borders and maintenance of mitochondria and cytosolic integrity.

The untreated kidney showed more severe tubule injuries indicated by loss of brush borders, apical blebbing, cytosolic vacuolization of the epithelial cells, as well as detachment and sloughing of the epithelial cells from basement membranes (yellow arrows, brush border; green arrows, epithelial cells sloughing into tubular lumen; blue arrows, mitochondria; brown arrows, cytoplasmic vacuolization and pink arrows, apical cytoplasm blebbing). The untreated kidney tissue also exhibited increased elongated and lysed mitochondria. On the contrary, the $3^{rd}$ forward synchronization modulation electric field treated kidney tissue showed relatively intact epithelial cells with preserved brush borders and maintenance of mitochondria and cytosolic integrity.

The studies on both the mouse KTX and human renal grafts indicated that $3^{rd}$ forward SMEF effectively preserved graft cell morphology and alleviated the tubular injury.

As such, in various embodiments, the present invention provides a system and method for controlling an active ion transporter by applying an energy generating synchronization modulation electric field, the $3^{rd}$ generation synchronization modulation electric field, which not only synchronizes the active ion transporter, for example, the Na/K pumps, but also drives the Na/K pump, when by consuming ATP molecule to actively transport Na and K ions, synthesizes ATP in each pumping cycle. The synchronization modulation electric field of the present invention has been shown to be effective in addressing ischemia.

The present invention may be embodied on various computing platforms that perform actions responsive to software-based instructions and most particularly on touchscreen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device. However, as indicated above, due to circuit statutory subject matter restrictions, claims to this invention as a software product are those embodied in a non-transitory software medium such as a computer hard drive, flash-RAM, optical disk or the like.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object-oriented programming language such as Java, C #, C++, Visual Basic or the like and conventional procedural programming languages, such as the "C" programming language or similar programming languages.

It should be emphasized that the above-described embodiments of the present disclosure are merely possible examples of implementations set forth for a clear understanding of the principles of the disclosure. Many variations and modifications can be made to the above-described embodiment(s) without departing substantially from the spirit and principles of the disclosure. All such modifications and variations are intended to be included herein within the scope of this disclosure and protected by the following claims.

What is claimed is:

1. A method for controlling active ion transporters for the treatment of kidney ischemia, the method comprising:

applying an oscillating electric field to one or more active ion transporters of a kidney experiencing ischemia, wherein the oscillating electric field comprises three serially applied phases and wherein applying the oscillating electric field comprises;

applying a synchronization phase to synchronize the active ion transporters to a physiological turnover rate of the active ion transporters down to individual steps within a running cycle with a net-consumption of adenosine triphosphate (ATP) substantially equal to zero, wherein applying the synchronization phase comprises, applying an oscillating electric field to synchronize an ion-pumping in half-cycle and an ion-extrusion half-cycle of the active ion transporters, wherein the ion-pumping in half-cycle of the active ion transporter is in a negative half-cycle and the ion-extrusion half-cycle of the active ion transporter is in a positive half-cycle of the oscillating electric field and wherein applying the synchronization phase further comprises, applying an activation overshoot electric pulse at a start of the negative half-cycle and at a start of the positive half-cycle of the oscillating electric field, applying an energy-trap overshoot electric pulse at an end of the negative half-cycle and at an end of the positive half-cycle of the oscillating electric field and applying an electric field plateau in between the activation overshoot electric pulse and the energy-trap overshoot electric pulse, wherein the activation overshoot electric pulse, the electric field plateau and the energy-trap overshoot electric pulse result in the synchronization of the active ion transporters down to individual steps within the running cycle;

applying a modulation phase to modulate the synchronized active ion transporters to a predetermined target turnover rate; and applying a maintenance phase to maintain the synchronized active ion transporters at the predetermined target turnover rate for a predetermined duration of time.

2. The method of claim 1, wherein one ATP molecule is consumed during the running cycle of the one or more active ion transporters and one ATP molecule is synthesized during the running cycle of the active ion transporters, resulting in the net-consumption of ATP of the active ion transporters being substantially equal to zero during the running cycle.

3. The method of claim 1, wherein the one or more active ion transporters is a Na/K pump.

4. The method of claim 1, wherein the synchronization phase further restricts an outward transporter current at the start of the activation overshoot electric pulse in the positive half-cycle and restricts an inward transporter current at the start of the activation overshoot electric pulse in the negative half-cycle of the oscillating electric field.

5. The method of claim 1, wherein a membrane potential of the active ion transporters is hyperpolarized in response to the activation overshoot electric pulse and the energy-trap overshoot electric pulse during the negative half-cycle of the oscillating electric field, and wherein the membrane potential of the active ion transporters is depolarized in response to the activation overshoot electric pulse and the energy-trap overshoot electric pulse during the positive half-cycle of the oscillating electric field.

6. The method of claim 1, wherein a magnitude of the activation overshoot electric pulse is sufficient to allow the active ion transporters to operate within a physiological range of a membrane potentials of the active ion transporters and wherein a magnitude of the energy-trap overshoot electric pulse is sufficient to allow the active ion transporters to operate within a physiological range of the membrane potentials of the active ion transporters.

7. The method of claim 1, wherein a duration of the activation overshoot electric pulse is about 1 ms or less, a magnitude of the activation overshoot electric pulse is at least about 90 mV, a duration of the energy-trap overshoot electric pulse is about 1.5 ms or less, a magnitude of the energy-trap overshoot electric pulse is about 70 mV and the electric field plateau is about 20 mV between the activation overshoot electric pulse and the energy-trap overshoot electric pulse.

8. The method of claim 1, wherein a frequency of the oscillating electric field during the synchronization phase is substantially equal to the physiological turnover rate of the active ion transporters.

9. The method of claim 1, wherein applying the modulation phase further comprises:
applying an oscillating electric field wherein waveform of the oscillating electric field is identical as the oscillating electric field in the synchronization phase, and the magnitude of the activation overshoot electric pulse and the energy-trap overshoot electric pulse is the same as the magnitude of the activation overshoot electric pulse and the energy-trap overshoot electric pulse in the synchronization phase, respectively, and the duration of the activation overshoot electric pulse and the energy-trap overshoot electric pulse is the same as the duration of the activation overshoot electric pulse and the energy-trap overshoot electric pulse in the synchronization phase, respectively.

10. The method of claim 1, wherein applying the modulation phase further comprises applying a forward modulation wherein a frequency of the oscillating electric field is increased to accelerate a turnover rate of the active ion transporters to the predetermined target turnover rate and applying a backward modulation wherein the frequency of the oscillating electric field is decreased to decelerate the active ion transporters to the predetermined target turnover rate.

11. The method of claim 10, wherein increasing and decreasing the frequency of the oscillating electric field is performed in a stepwise pattern, where the frequency is changed from about 3% to about 10% and repeated for approximately 5 to 10 oscillating pulses at the frequency.

12. The method of claim 1, wherein applying the maintenance phase comprises applying a waveform and a frequency of the oscillating electric field that is equivalent to a waveform and a frequency of the oscillating electric field applied during the modulation phase.

13. The method of claim 1, wherein the ischemia is selected from warm ischemia and cold ischemia.

14. A system for controlling active ion transporters for the treatment of kidney ischemia, the system comprising:
an electric field generator to generate and apply an oscillating electric field to one or more active ion transporters of a kidney experiencing ischemia, wherein the oscillating electric field comprises three serially applied phases and applying the oscillating electric field comprises;
applying a synchronization phase to synchronize the active ion transporters to a physiological turnover rate of the active ion transporter down to individual steps within a running cycle with a net-consumption of adenosine triphosphate (ATP) substantially equal to zero, wherein applying the synchronization phase comprises, applying an oscillating electric field to synchronize an ion-pumping in half-cycle and an ion-extrusion half-cycle of the active ion transporters, wherein the ion-pumping in half-cycle of the active ion transporter is in a negative half-cycle and the ion-extrusion half-cycle of the active ion transporter is in a positive half-cycle of the oscillating electric field and wherein applying the synchronization phase further comprises, applying an activation overshoot electric pulse at a start of the negative half-cycle and at a start of the positive half-cycle of the oscillating electric field, applying an energy-trap overshoot electric pulse at an end of the negative half-cycle and at an end of the positive half-cycle of the oscillating electric field and applying an electric field plateau in between the activation overshoot electric pulse and the energy-trap overshoot electric pulse, wherein the activation overshoot electric pulse, the electric field plateau and the energy-trap overshoot electric pulse result in the synchronization of the active ion transporters down to individual steps within the running cycle;
applying a modulation phase to modulate the synchronized active ion transporters to a predetermined target turnover rate; and
applying a maintenance phase to maintain the synchronized active ion transporters at the predetermined target turnover rate for a predetermined duration of time.

15. The system of claim 14, wherein one ATP molecule is consumed during the running cycle of the active ion transporters and one ATP molecule is synthesized during the running cycle of the active ion transporters, resulting in the net-consumption of ATP of the active ion transporters being substantially equal to zero during the running cycle.

16. The method of claim 14, wherein the one or more active ion transporters is a Na/K pump.

17. A non-transitory computer-readable medium storing a set of instructions configured for being executed by at least one processor for performing a method for controlling one or more active ion transporters of a kidney experiencing ischemia, the method comprising: controlling an electric field generator to apply an oscillating electric field to the one or more active ion transporters, wherein the oscillating electric field comprises three serially applied phases and wherein applying the oscillating electric field comprises;

applying a synchronization phase to synchronize the active ion transporters to a physiological turnover rate of the active ion transporters down to individual steps within a running cycle with a net-consumption of adenosine triphosphate (ATP) substantially equal to zero, wherein applying the synchronization phase comprises, applying an oscillating electric field to synchronize an ion-pumping in half-cycle and an ion-extrusion half-cycle of the active ion transporters, wherein the ion-pumping in half-cycle of the active ion transporter is in a negative half-cycle and the ion-extrusion half-cycle of the active ion transporter is in a positive half-cycle of the oscillating electric field and wherein applying the synchronization phase further comprises, applying an activation overshoot electric pulse at a start of the negative half-cycle and at a start of the positive half-cycle of the oscillating electric field, applying an energy-trap overshoot electric pulse at an end of the negative half-cycle and at an end of the positive half-cycle of the oscillating electric field and applying an electric field plateau in between the activation overshoot electric pulse and the energy-trap overshoot electric pulse, wherein the activation overshoot electric pulse, the electric field plateau and the energy-trap overshoot electric pulse result in the synchronization of the active ion transporters down to individual steps within the running cycle;

applying a modulation phase to modulate the synchronized active ion transporters to a predetermined target turnover rate; and applying a maintenance phase to maintain the synchronized active ion transporters at the predetermined target turnover rate for a predetermined duration of time.

18. The media of claim 17, wherein one ATP molecule is consumed during the running cycle of the active ion transporters and one ATP molecule is synthesized during the running cycle of the active ion transporters, resulting in the net-consumption of ATP of the active ion transporters being substantially equal to zero during the running cycle.

* * * * *